United States Patent
Luusua et al.

(10) Patent No.: US 6,705,758 B1
(45) Date of Patent: Mar. 16, 2004

(54) STEERING ARRANGEMENT FOR MOBILE X-RAY APPARATUS

(75) Inventors: Jarmo Luusua, Vantaa (FI); Petri Pohjoispuro, Espoo (FI); Petri Pyrrö, Lahela (FI)

(73) Assignee: Instrumntarium Corp., Helsinki (FI)

( * ) Notice: Subject to any disclaimer, the term of this patent is extended or adjusted under 35 U.S.C. 154(b) by 0 days.

(21) Appl. No.: 10/018,987

(22) PCT Filed: Jun. 16, 2000

(86) PCT No.: PCT/FI00/00543
§ 371 (c)(1),
(2), (4) Date: May 1, 2002

(87) PCT Pub. No.: WO01/01860
PCT Pub. Date: Jan. 11, 2001

(30) Foreign Application Priority Data

Jun. 30, 1999 (FI) ................................................... 991487

(51) Int. Cl.$^7$ ................................................. H01J 31/49
(52) U.S. Cl. ...................... 378/198; 378/102; 378/193; 180/6.2; 180/6.48; 180/6.5
(58) Field of Search ................................ 378/198, 102, 378/193, 197, 19, 196; 180/6.2, 6.48, 6.5, 6.28, 19.2, 19.3

(56) References Cited

U.S. PATENT DOCUMENTS

| 4,165,461 A | 8/1979 | Ishijima ...................... 250/359 |
| 4,341,279 A | 7/1982 | Waerve |
| 4,697,661 A | 10/1987 | Pajerski et al. ............... 180/6.5 |
| 5,067,145 A | * 11/1991 | Siczek et al. ............... 378/198 |
| 5,081,662 A | * 1/1992 | Warden et al. ............... 378/198 |
| 5,351,282 A | 9/1994 | Kadowaki et al. ........... 378/198 |
| 5,425,069 A | 6/1995 | Pellegrino et al. ........... 378/198 |
| 5,436,950 A | 7/1995 | Pauli et al. ..................... 378/4 |
| 5,511,106 A | 4/1996 | Doebert et al. ............. 378/146 |
| 5,550,886 A | 8/1996 | Dobbs et al. ................. 378/19 |
| 5,835,558 A | * 11/1998 | Maschke .................... 378/198 |
| 6,094,469 A | 7/2000 | Dobbs et al. ................. 378/19 |
| 6,104,780 A | * 8/2000 | Hanover et al. ............... 378/92 |
| 6,139,183 A | * 10/2000 | Graumann ................... 378/206 |
| 6,374,937 B1 | * 4/2002 | Galando et al. ............ 180/211 |

* cited by examiner

Primary Examiner—Craig E Church
Assistant Examiner—Irakli Kiknadze
(74) Attorney, Agent, or Firm—Andrus, Sceales, Starke & Sawall, LLP

(57) ABSTRACT

A mobile X-ray apparatus has a carriage provided with at least one pair of independently driven driving wheels and a motor. The carriage includes a driving handle, which comprises sidebars, attached to a rotation axis solidly fixed to the carriage, and a crossbar, which is connected to the sidebars in an articulated manner to allow the turning movement of the sidebars about the said axis independently of each other. The apparatus also controls the operation of the motor by movements of the handle. The sidebars are provided with a toothed rim that moves along with the movement of the respective sidebar. The movements are measured by a potentiometer, which converts the movement into an electric signal by which the motor of the driving wheels is controlled.

5 Claims, 1 Drawing Sheet

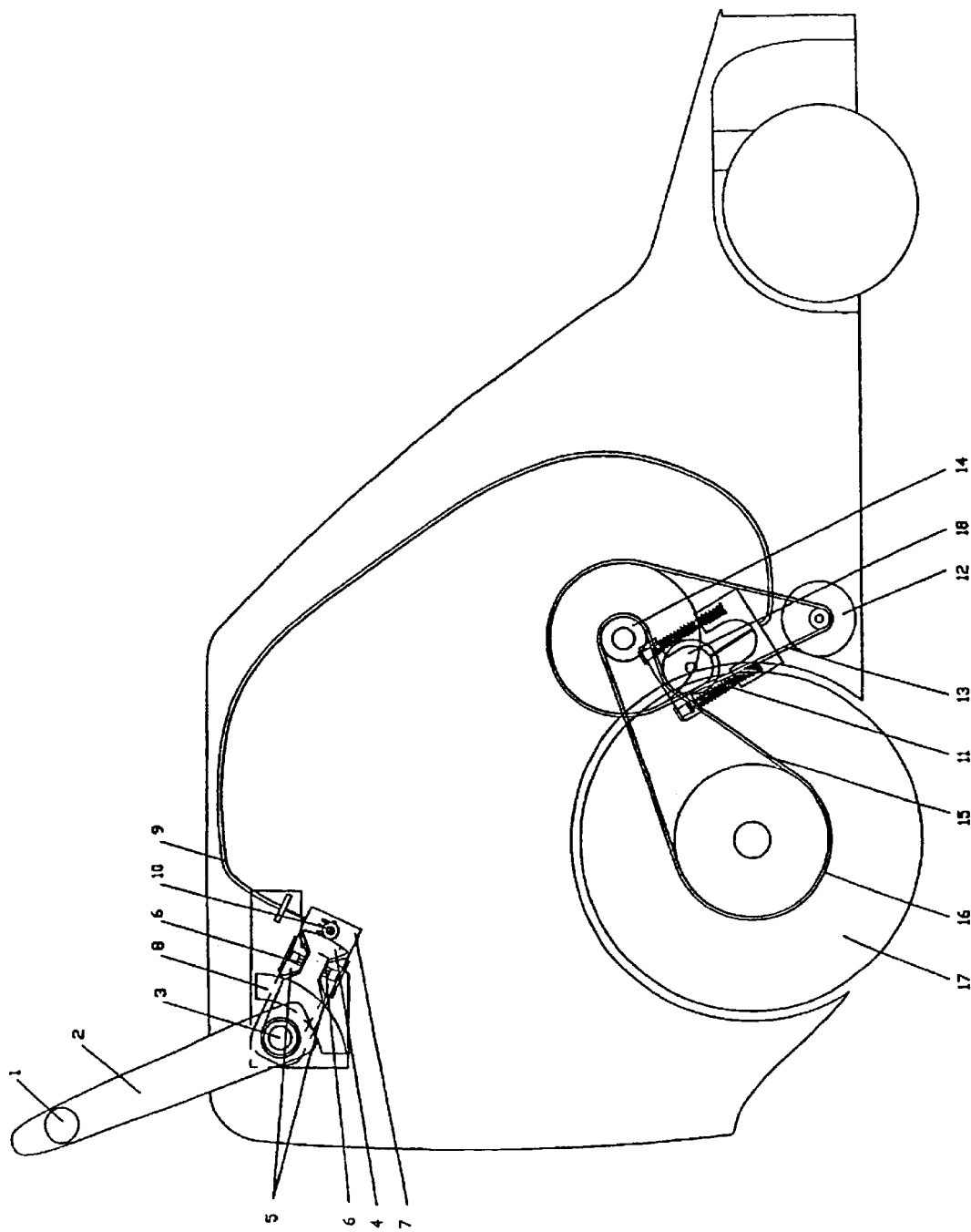

STEERING ARRANGEMENT FOR MOBILE X-RAY APPARATUS

CROSS REFERENCE TO RELATED APPLICATION

The present application is the U.S. national stage application of International Application PCT/FI00/00543, filed Jun. 16, 2000, which international application was published on Jan. 11, 2001 as International Publication WO 01/01860 in the English languages. The International Application claims priority of Finnish Patent application Ser. No. 991487, filed Jun. 30, 1999.

SUMMARY OF THE INVENTION

The present invention relates to a mobile X-ray apparatus which comprises a carriage provided with at least one pair of independently driven driving wheels and their motor means, the carriage including a driving handle which comprises side bars and a crossbar extending between them, the said apparatus in addition comprising means responsive to the movement of the driving handle, which responsive means control the operation of the motor means in order to steer the carriage in the desired direction.

The mobile X-ray apparatus comprises a carriage to which is connected an X-ray source, X-ray receiving means and the control electronics required, and possibly a monitor for immediate examination of, for example, digitally produced X-ray photographs. When accumulators are used as the power source of a mobile X-ray apparatus, the weight of the apparatus increases and may be, for example, of the order of 300 kg, which means that to make the apparatus lighter to move, the driving motion must be motorised. One way of controlling this type of a motorised X-ray apparatus is to provide a driving handle, the manual moving of which provides control signals for driving the motor means of the driving wheels of the carriage, in order to steer the carriage in the desired direction. One such solution is disclosed in U.S. Pat. No. 4,697,661, in which the operation of the driving handle is based on converting the movement of the driving handle into a bending movement of the cantilevered arms arranged in the vicinity of the driving handle, the bending movement causing the said control signals to be produced. One object of the present invention is to achieve a new type of mobile X-ray apparatus in which the movement of the driving handle can be converted relatively simply and reliably into an electric signal controlling the control electronics of the motor means. An important additional object is to provide a motorised mobile X-ray apparatus which is additionally arranged to be manually movable without the motor means in exceptional situations.

BRIEF DESCRIPTION OF THE INVENTION

In order to achieve the objects of the invention, the mobile X-ray apparatus relating to the invention is characterised in that the side bars of the driving handle are attached to a rotation axis solidly fixed to the carriage, so as to turn about the axis; that the side bars and the crossbar are connected to each other in an articulated manner to allow the turning movement of the side bars about the said rotation axis to different extents and/or in different directions; that the side bars are provided with means which move along with the turning movement of the respective side bar each time, and the movement of which means is measured by measuring means which convert the movement of the said means into an electric signal by means of which the operation of the motor means of the driving wheels is controlled.

BRIEF DESCRIPTION OF THE DRAWINGS

The invention is described in greater detail below, with reference to the appended drawing, the only FIGURE of which shows a diagrammatic side view of the carriage part of the X-ray apparatus, without the actual X-ray imaging devices to be included in it.

DETAILED DESCRIPTION OF THE INVENTION

In accordance with the figure, the carriage comprises driving wheels 17, of which there is one on either side of the carriage and which are driven each time by means of a driving motor 12 via belts 13, 15. Belt 15 is tightened by means of tension springs 11 and a jockey pulley 18 connected to them for transmitting the rotary movement of the driving motor 12 via the belt pulleys 14, 16 to the driving wheel 17. The operation of the driving motor 12 is controlled by means of a driving handle which comprises side bars 2 and a crossbar 1 attached between them in an articulated manner. The side bars 2 are attached to a rotation axis 3 solidly fixed to the carriage to make possible their turning movement about the rotation axis 3. In the embodiment shown, to the rotation axis 3 end of the side bars is connected a part 4 of a toothed rim which moves together with the side bar 2 during the turning movement. This turning movement of the toothed rim 4 is measured, for example, by measuring means 10 realised as a potentiometer, which means converts the said movement into an electric signal which is fed to the control electronics of the driving motors 12 in order to drive the driving motors to steer the carriage in the desired direction. The articulated joint between the side bars 2 and the crossbar 1 allows a turning movement of the side bars 2 to a different extent and, if necessary, in a different direction about the said rotation axis 3 in order to make possible the desired direction of travel. When driving straight (forwards or backwards), the driving wheels rotate at mutually the same speed and in the same direction, but when turning left or right, one of the driving wheels must rotate slower than the driving wheel on the other side, or the driving wheels must rotate in different directions.

In case of an exceptional situation, for example, when power is not switched on to the apparatus or if the batteries have ran down, the X-ray apparatus carriage relating to the invention is provided with means by which the driving motors 12 can be released from being driven together with the driving wheels 17 to allow the apparatus to be moved manually. In the embodiment shown, these means include a release plate 7 to which is attached a wire cable 9 which is connected to the jockey pulley 18 of the drive belt 15. When the driving handle is pushed or pulled considerably beyond the normal driving motion, the release plate 7 pulls the wire cable 9 which in turn pulls the jockey pulley 18, thus allowing the drive belt 15 to slide over the belt pulley 14. This means that when the carriage is pushed or pulled, the wheels 17 are able to rotate although the drive motor 12 is at a halt by itself. When released from the driving handle, the tension springs 11 press the jockey pulley 18 against the drive belt 15, whereby the releasing of the driving handle acts as a brake due to the drive motor being at a halt by itself. When the driving handle is pulled into the normal position, it locks in it. The normal driving motion of the driving handle is restricted by means of limit stops 5 and the movement of the release means is for its part restricted by means of a stopper plate 8. In connection with the toothed rim 4 are in addition preferably arranged spring members 6 which position the driving handle in its centre position when the grip on the drive handle is released. The height of the driving handle is preferably arranged so as to be adjustable.

We claim:

1. A mobile X-ray apparatus comprising:

a carriage having at least one pair of independently driven driving wheels;

motor means (12) for driving the driving wheels;

a driving handle comprising a pair of spaced side bars (2) rotatably coupled to the carnage along an axis of rotation (3) and a cross bar movable with said side bars (1), said cross bar being coupled to and extending between the side bars in an articulated manner to allow turning movement of the respective side bars to different extents and in different directions about the axis; and means that move with each turning movement of each respective side bar (2), the movement of said means being measured by a measuring means (10) which convert the measured movement into electric signals; and control means receiving the electric signals for controlling the motor means responsive to the electrical signals to steer the carriage in a desired direction.

2. An X-ray apparatus as claimed in claim 1, further comprising means (6) for positioning the driving handle (1, 2) automatically in a centre position when the grip on the driving handle is released.

3. An X-ray apparatus as claimed in claim 1, wherein the height of the driving handle (1, 2) is adjustable.

4. An X-ray apparatus as claimed in claim 1, further comprising release means (7–9) operable by movement of said driving handle to release the motor means from a driving coupling with the driving wheels (17), allowing the wheels (17) to rotate freely and thus allow manual movement of the carriage.

5. An X-ray apparatus as claimed in claim 2, wherein the height of the driving handle (1,2) is adjustable.

* * * * *